US007195015B2

(12) United States Patent
Kuriyama

(10) Patent No.: US 7,195,015 B2
(45) Date of Patent: Mar. 27, 2007

(54) BREATHING APPARATUS

(75) Inventor: Satoshi Kuriyama, Kita-ku (JP)

(73) Assignee: Koken, Ltd., Tokyo (JP)

( * ) Notice: Subject to any disclaimer, the term of this patent is extended or adjusted under 35 U.S.C. 154(b) by 447 days.

(21) Appl. No.: 10/482,272

(22) PCT Filed: Apr. 8, 2002

(86) PCT No.: PCT/JP02/03484

§ 371 (c)(1), (2), (4) Date: Dec. 29, 2003

(87) PCT Pub. No.: WO03/002205

PCT Pub. Date: Jan. 9, 2003

(65) Prior Publication Data

US 2004/0168689 A1 Sep. 2, 2004

(30) Foreign Application Priority Data

Jun. 29, 2001 (JP) ....................................... 2001-198494

(51) Int. Cl.
*A62B 7/10* (2006.01)
*A61M 16/00* (2006.01)

(52) U.S. Cl. ............................ 128/205.12; 128/206.12; 128/204.21; 128/205.23; 128/206.15

(58) Field of Classification Search ............ 128/204.26, 128/204.18, 204.23, 201.25, 202.22, 205.23, 128/205.25, 205.27, 205.29, 206.12, 206.15, 128/205.18, 204.21, 205.12
See application file for complete search history.

(56) References Cited

U.S. PATENT DOCUMENTS 4,430,995 A * 2/1984 Hilton ................... 128/204.21
4,590,951 A 5/1986 O'Connor
4,886,056 A * 12/1989 Simpson ................ 128/201.25
4,899,740 A * 2/1990 Napolitano ............ 128/202.22
4,971,052 A 11/1990 Edwards
5,036,842 A * 8/1991 van der Smissen et al. ...... 128/204.18
5,297,544 A * 3/1994 May et al. ............. 128/202.22
5,318,020 A * 6/1994 Schegerin .............. 128/205.12
5,322,058 A * 6/1994 Pasternack ............. 128/204.28
5,413,097 A * 5/1995 Birenheide et al. ..... 128/206.17
5,577,496 A * 11/1996 Blackwood et al. ... 128/201.25
5,906,203 A * 5/1999 Klockseth et al. ...... 128/205.24
5,950,621 A * 9/1999 Klockseth et al. ...... 128/204.26
6,135,106 A 10/2000 Dirks et al.

FOREIGN PATENT DOCUMENTS

EP 0 130 707 A2 1/1985
EP 0 352 938 A2 1/1990
GB 2209474 A * 5/1989
JP 60-68869 4/1985
JP 10-118183 5/1998

* cited by examiner

*Primary Examiner*—Henry Bennett
*Assistant Examiner*—Mital Patel
(74) *Attorney, Agent, or Firm*—McDermott Will & Emery LLP

(57) ABSTRACT

An inhalation opening 6 and an exhalation-opening 4 are formed in the facepiece 2 of a breathing apparatus 1 and the openings can be closed with an inhalation valve 8 and exhalation valve 7, respectively. If a person wearing the breathing apparatus 1 inhales, the inhalation valve 8 is open and the exhalation valve 7 is closed. A photointerrupter 11 senses the closing operation of the exhalation valve 7 and supplies electric power to a motor 9 to drive a blower 16.

3 Claims, 7 Drawing Sheets

BREATHING APPARATUS

BACKGROUND OF THE INVENTION

1. Field of the Invention

The present invention relates to a breathing apparatus suitable for full-face masks and half-face masks used with the object of protecting from dust, gases, and the like.

2. Description of the Related Art

People working in the atmosphere containing hazardous dust or toxic gases usually wear a dust mask or a gas mask and inhale a purified air after the hazardous and toxic substances contained in the air have been removed-with a filtration material such as active carbon or a filter contained in the dust mask.

However, filtration materials such as filters, absorption canisters, and the like, with good purification efficiency typically have a large draft resistance.

In particular, because penetration of radioactive dust present in nuclear power plants, dioxin-containing toxic dust in decomposition sites of incinerators, and toxic gases generated in a variety of other industrial operations into a human body affects human health, filtration materials with a high purification efficiency and, therefore, a high draft resistance are used for dust masks. People wearing dust masks provided with such filtration materials have difficulty in breathing normally by using only the capacity of their lungs.

Accordingly, a blower operated by electric power has been mounted on a dust mask in front or behind the filtration material in a draft channel and the suction force created by the rotation of the blower facilitated breathing.

However, the following problems are associated with such conventional technology.

(1) Toxic substances penetrate into the human body via trachea essentially only during inhalation. Therefore, the filtration material may operate only during inhalation.

In the dust masks comprising no blower, because the exhaled air is let out by an exhalation valve, the filtration material is not exhausted during exhalation. On the other hand, since in the dust masks equipped with a blower, the blower operates also during exhalation, the filtration material is exhausted faster than in the dust mask comprising no blower.

(2) Human breathing requires 0.45 to 0.68 L of air for a single inhalation of an adult person. The frequency of inhalation is typically about 12 to 16 per minute. In particular, masks are used most often during work and the breathing volume increases in proportion to the volume of work. The maximum draft volume during inhalation can be higher than 85 L/min at the peak.

However, if the voltage supplied to the blower is set such that the ventilation amount of the blower is no less than the maximum draft volume, the electric power consumed by the blower unnecessarily increases and the exhaustion of the filtration material is accelerated. Further, because the filtration materials with a high draft resistance require blowers with a high torque, the consumption of electric power increases in proportion to the draft resistance of the filtration material used.

(3) In the conventional dust masks equipped with a blower, the air is supplied into the dust mask also during exhalation. As a result, a positive pressure is created in the facepiece of the dust mask. In particular, if the ventilation volume of the blower is set higher than the maximum peak of breathing, the pressure in the facepiece becomes very high and the exhalation resistance is increased.

On the other hand, in the conventional dust masks comprising no blower, the exhalation resistance is practically equal to the exhalation valve resistance, and the exhalation resistance is typically lower than that in the above-described dust masks equipped with a blower.

A breathing apparatus (mask for breathing) comprising a fan driven by a motor, a filter arranged opposite the fan, and a mask facepiece receiving the air that passed through the filter has been disclosed in Japanese Patent Application Laid-open No. H2-74267 (and in the U.S. Pat. No. 4,971,053 corresponding thereto). This breathing apparatus also comprises a differential pressure sensor composed of a pressure-responsive member (diaphragm) connected so that one side thereof faces the pressure downstream of the fan and the other side faces the pressure upstream of the fan, and control means for controlling the operation of the fan motor in response to the differential pressure sensor.

However, in such a breathing apparatus, the first channel connecting one side of the pressure-responsive member to the zone downstream of the fan and the second channel connecting the other side of the pressure-responsive member to the zone upstream of the fan have to be provided separately from the main inhalation channel. As a result, the mask structure is very complex and the differential pressure sensor is difficult to mount in a compact manner. Further, because the opening of the first channel or second channel had to be provided between the filter and the fan, the size of the entire breathing apparatus was inevitably increased. Further, a diaphragm is used as the pressure-responsive member, but the diaphragm is easily fatigued or damaged and the set values of the reaction pressure of the differential pressure sensor are difficult to maintain.

SUMMARY OF THE INVENTION

It is an object of the present invention to provide a breathing apparatus with a simple structure and not liable to breakdown, in which the increase in the exhaustion of the filtration material and electric power consumed by the motor, which drives the blower, can be suppressed and the exhalation resistance can be reduced.

In order to attain this object, the present invention provides a breathing apparatus comprising a facepiece with an inhalation opening and an exhalation opening formed therein, an inhalation valve disposed adjacent to the inhalation opening so as to be open during inhalation and closed during exhalation, an exhalation valve disposed adjacent to the exhalation opening so as to be closed during inhalation and opened during exhalation, a blower for blowing the outside air into the facepiece through the inhalation opening, and a sensor which is sensitive to the opening or closing operation of the exhalation valve or inhalation valve. If the sensor detects that the inhalation valve has been opened or that the exhalation valve has been closed, electric power is supplied to the motor, which drives the blower, the blower is activated, and the outside air is forcibly introduced into the facepiece.

The sensor comprises a photointerrupter disposed in the vicinity of the exhalation valve or inhalation valve and sensing the position of the exhalation valve or inhalation valve. Alternatively, the sensor comprises the exhalation valve or inhalation valve formed from an electrically conductive material and a valve seat from an electrically conductive material secured to the facepiece, and detects that the exhalation valve or inhalation valve has been closed by sensing the electric current from the exhalation valve or inhalation valve to the valve seat.

The motor serving to drive the blower operates in a normal mode only during inhalation and does not operate or operates at a low speed during exhalation, based on the signals from the sensor. Therefore, the exhaustion of the filtration material and power consumption by the motor can be reduced. Moreover, the risk of pressure rising inside the facepiece and exhalation resistance increasing during exhalation is eliminated.

In the breathing apparatus in accordance with the present invention, control signals for the motor are generated using the operation of the exhalation valve or inhalation valve originally provided in the breathing apparatus. Therefore, the structure is simple and parts that are brittle or easy to deform, such as the diaphragms, are not required which results in improved resistance to breakdown.

DESCRIPTION OF THE PREFERRED EMBODIMENTS

The first embodiment of the present invention will be described hereinbelow with reference to FIGS. 1 through 4.

Figure 1:
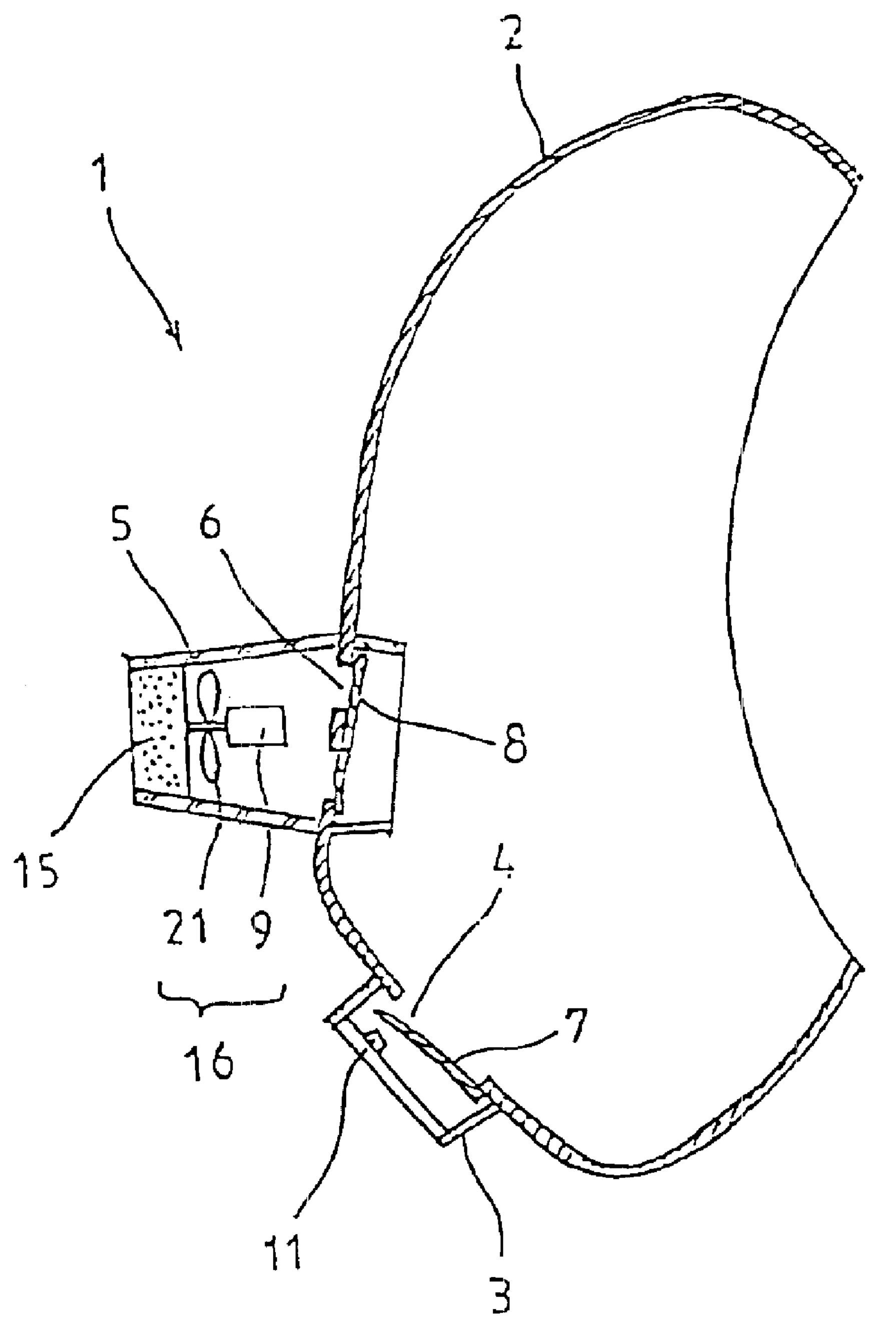
FIG. 1 is a cross-sectional view of the breathing apparatus according to a first embodiment of the present invention.

As shown in FIG. 1, an exhalation opening 4 and an inhalation opening 6 are formed in a facepiece 2 of a breathing apparatus 1. The exhalation opening 4 is covered on the outer surface thereof with an exhalation valve cover 3 provided on the facepiece 2.

Further, the inhalation opening 6 is covered on the outer surface thereof with a filtration material cover 5 provided on the facepiece 2.

An exhalation valve 7 which is open during exhalation and closed during inhalation is provided in the exhalation opening 4. On the other hand, an inhalation valve 8 which is closed during exhalation and open during inhalation is provided in the inhalation opening 6.

A filtration material 15 and a blower 16 are disposed opposite each other inside the filtration material cover 5 on the outer side of the inhalation valve 8. The blower 16 is composed of an impeller 21 and a motor 9 for rotationally driving the impeller 21. The shaft of the impeller 21 is directly connected to the output shaft of the motor 9. If the motor 9 is activated and the impeller 21 is rotated, the outer air passes through the filtration material 15 and is blown inside of the facepiece 2 via the inhalation opening 6.

The operation of a photointerrupter 11, which follows the operation of the exhalation valve 7 will be described below with reference to FIG. 2 and FIG. 3.

An exhalation valve seat 10 is mounted on the periphery of the exhalation opening 4 of the facepiece 2, and the exhalation valve 7 is mounted on the exhalation valve seat 10. Further, a sensor composed of the photointerrupter 11 which is sensitive to the movement of the exhalation valve 7 is disposed on the outer side of the exhalation valve 7 in the position close to the exhalation valve 7.

The photointerrupter 11 comprises a light-emitting diode 12 and a transistor receiver 13. The light-emitting surface of the light-emitting diode 12 and the light-receiving surface of the transistor receiver 13 face the exhalation valve 7. If the IR radiation that was output from the light-emitting diode 12 is received by the transistor receiver 13, the photointerrupter 11 generates a signal.

Figure 2:
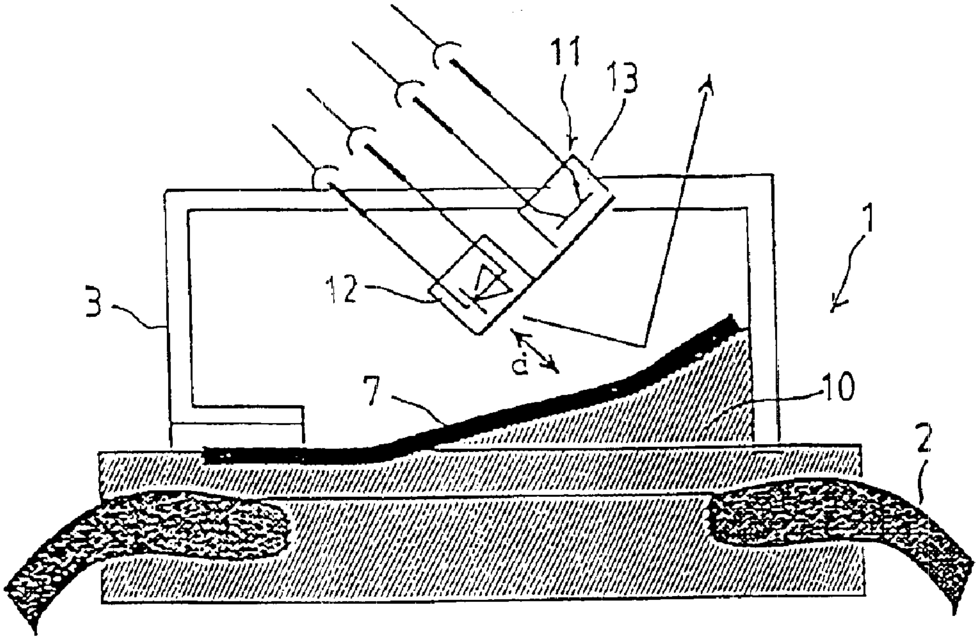
FIG. 2 is a cross-sectional view of the principal part of the breathing apparatus shown in FIG. 1, illustrating the state in which the exhalation valve is closed.

When the person wearing the breathing apparatus 1 inhales, the exhalation valve 7 comes in tight contact with the exhalation valve seat 10, as shown in FIG. 2. As a result, the exhalation valve 7 recedes from the photointerrupter 11 at no less than the set distance d. Accordingly, the IR radiation that was output from the light-emitting diode 12 and reflected by the exhalation valve 7 does not fall on the light-receiving surface of the transistor receiver 13 and, therefore, no signal is generated by the photointerrupter 11.

Figure 3:
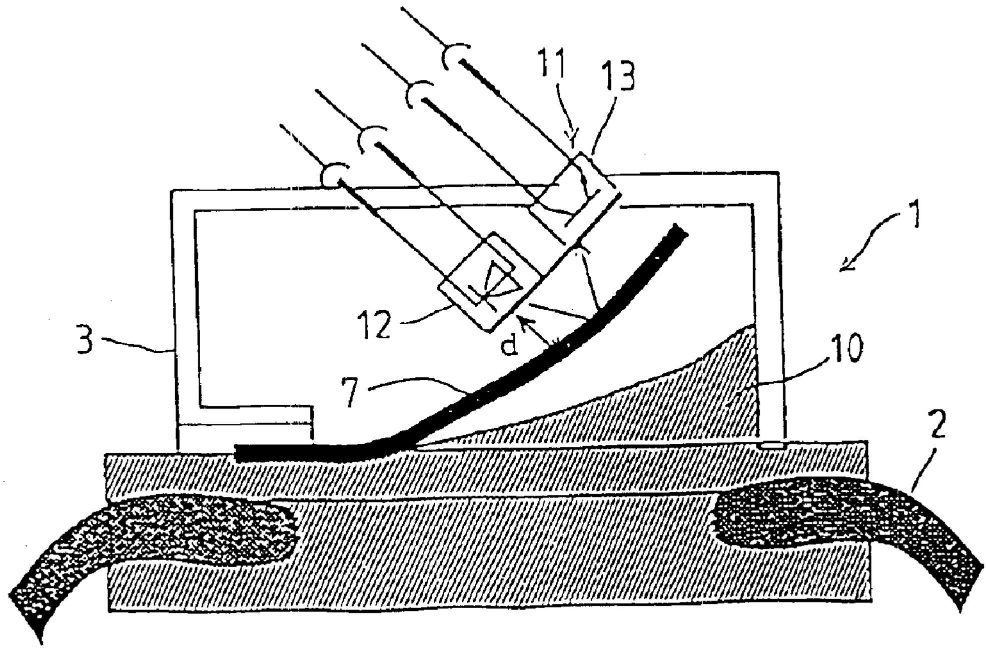
FIG. 3 is a cross-sectional view of the principal part of the breathing apparatus shown in FIG. 1, illustrating the state in which the exhalation valve is open.

On the other hand, when the person wearing the breathing apparatus 1 exhales, the exhalation valve 7 recedes from the exhalation valve seat 10 and approaches the photointerrupter 11, as shown in FIG. 3. As a result, the distance from the exhalation valve to the photointerrupter 11 becomes less than the set distance d. In such a case, the IR radiation that was output from the light-emitting diode 12 and reflected by the exhalation valve 7 falls on the light-receiving surface of the transistor receiver 13. As a result, the photointerrupter 11 generates a signal.

Figure 4:
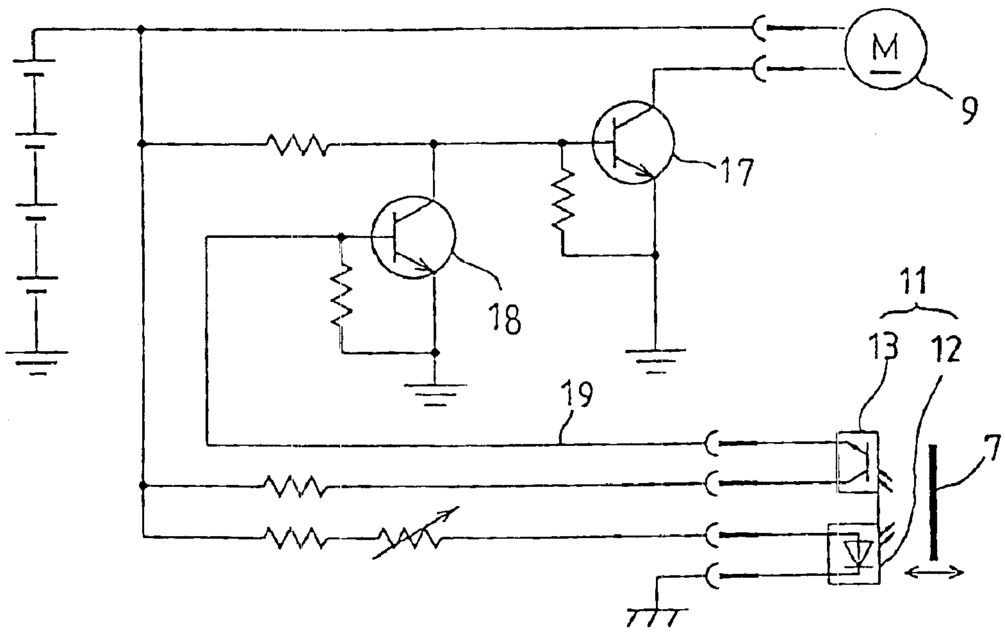
FIG. 4 is the diagram of a circuit for controlling the supply of power to the motor for driving the blower.

The circuit for supplying electric power to the motor 9 for driving the impeller 21 constituting the blower 16 will be explained below with reference to FIG. 4.

A first transistor 17 is connected to a second transistor 18 and the operation of the first transistor is controlled by the second transistor 18. The second transistor 18 is connected to the transistor receiver 13 of the photointerrupter 11 via a conductor 19.

When the exhalation valve 7 is closed and the IR radiation that was output from the light-receiving diode 12 and reflected by the exhalation valve 7 does not fall on the transistor receiver 13, the transistor receiver 13 generates no output. Therefore, the second transistor 18 is not actuated. For this reason, the operation of the first transistor 17 is not controlled. As a result, because the first transistor 17 operates so as to supply electric power to the motor 9, the motor 9 operates in a usual mode and drives the blower 16, thereby introducing the outside air inside the facepiece 2 through the inhalation opening 6.

On the other hand, when the exhalation valve 7 is open and the IR radiation that was output from the light-receiving diode 12 and reflected by the exhalation valve 7 falls on the transistor receiver 13, the output of the transistor receiver 13 is supplied to the second transistor 18 via the conductor 19 and the second transistor 18 is actuated. As a result, the operation of the first transistor 17 is controlled and the first transistor 17 limits power supply to the motor 9. As a consequence, blowing of the blower 16 is slowed down or is terminated.

The second embodiment of the present invention will be described below with reference to FIG. 5.

The inner surface of the inhalation opening 6 formed in the facepiece 2 of the breathing apparatus is covered with the inhalation valve cover 20 provided on the facepiece 2. The inhalation valve 8 is disposed inside the inhalation valve cover 20. During inhalation, the inhalation valve 8 moves so as to recede from the inhalation opening 6 and introduces the outside air through the inhalation opening 6. During exhalation, the valve moves so as to approach the inhalation opening 6, comes in tight contact with the inhalation opening 6, and closes the inhalation opening 6.

The photointerrupter 11 is mounted on the surface of the inhalation valve cover 20 which faces the inhalation valve 8. The photointerrupter 11 is composed of a light-emitting diode and a transistor receiver, similarly to the first embodiment.

If the inhalation valve 8 is open and approaches the surface of the inhalation valve cover 20 where the photointerrupter 11 is located, that is, if the distance between the inhalation valve 8 and photointerrupter 11 becomes close to the prescribed distance d, the IR radiation that was output from the light-emitting diode and reflected by the inhalation valve 8, falls on the transistor receiver. As a consequence, the above-mentioned transistor receiver that has received the IR radiation generates an output which causes the motor 9 to execute normal operation and to drive the blower 16, thereby blowing the air through the inhalation opening 6 into the facepiece 2.

On the other hand, if the inhalation valve 8 is closed, the distance between the inhalation valve 8 and photointerrupter 11 exceeds the preset distance d, and the IR radiation that was output from the light-emitting diode and reflected by the inhalation valve 8 does not fall on the transistor receiver. As a result, the transistor receiver generates no output. As a consequence, blowing of the blower 16 is slowed down or is terminated.

In the present embodiment, as described hereinabove, when the inhalation valve 8 is open and the distance to the photointerrupter 11 decreases, the transistor receiver receives the IR radiation, whereas when the inhalation valve 8 is closed and the distance to the photointerrupter 11 is increased, the transistor receiver does not receive the IR radiation. Conversely, it is also possible that the transistor receiver receives no IR radiation when the inhalation valve is open and the distance to the photointerrupter 11 is decreased, whereas the transistor receiver receives the IR radiation when the inhalation valve 8 is closed and the distance to the photointerrupter 11 is increased. In such a case, the relationship between the reception of IR radiation by the transistor receiver and control of the motor 9 for driving the blower is identical to that of the first embodiment and the circuit shown in FIG. 4 can be used as is.

Further, in another possible configuration, the light-emitting surface of the light-emitting diode and the light-receiving surface of the transistor receiver are disposed opposite each other via a certain clearance, and only when the inhalation valve 8 is closed or only when it is open to a certain degree, at least part of the inhalation valve 8 is introduced between the light-emitting diode and transistor receiver, and the light that was output from the light-emitting diode is shielded and does not reach the transistor receiver. As a result, the photointerrupter can send a signal corresponding to the position of the inhalation valve 8 to the second transistor 18 (FIG. 4) for driving the motor.

Figure 5:
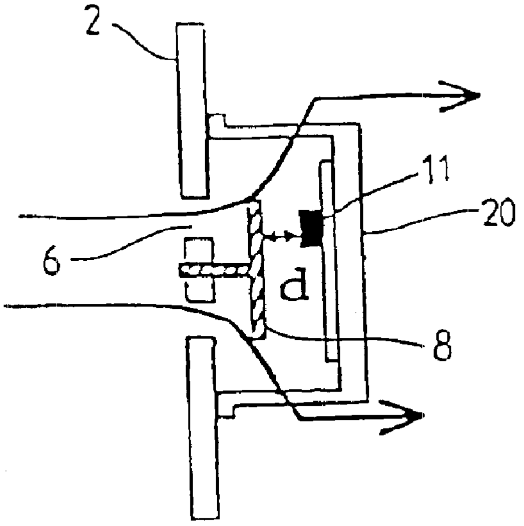
FIG. 5 is a cross-sectional view of the principal part of the breathing apparatus according to a second embodiment of the present invention, for explaining the structure for detecting the switching operation of the inhalation valve.

Further, in the example shown in FIG. 5, the photointerrupter 11 was arranged in the position facing the surface of the inhalation valve 8. However, the photointerrupter 11 may be instead arranged around the inhalation valve 8, such an arrangement enabling the photointerrupter 11 to sense the movement of the end surface of the inhalation valve 8.

Figure 6:
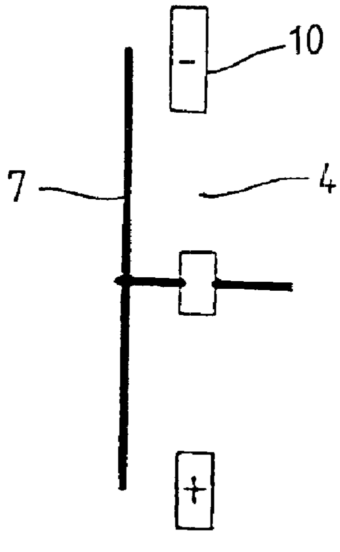
FIG. 6 is a cross-sectional view of the principal part of the breathing apparatus according to a third embodiment of the present invention, for explaining the structure for detecting the switching operation of the exhalation valve.

The third embodiment of the present invention will be described below with reference to FIG. 6.

Both the exhalation valve 7 and the exhalation valve seat 10 are formed from an electrically conductive material such as an electrically conductive rubber or the like or from an electrically conductive material subjected to processing inducing electric conductivity. The exhalation valve seat 10 is mounted on the facepiece of the breathing apparatus upon splitting into at least two parts. A plus pole is formed on one of the two parts of the exhalation valve seat 10 and a minus pole is formed on the other part.

The exhalation valve seat 10 functions as a sensor sensitive to the movement of the exhalation valve 7. During inhalation, the exhalation valve 7 is closed and brought in contact with the exhalation valve seat 10. In this state, the plus pole and minus pole of the exhalation valve seat 10 are connected to each other via the exhalation valve 7, causing electric current (signal) to flow. As a result, electric power is supplied to the motor 9, the motor 9 operates in a normal mode, and ventilation is conducted by the blower 16.

On the other hand, during exhalation, the exhalation valve 7 is open and separated from the exhalation valve seat 10. Therefore, no signal is generated. As a result, power supply to the motor 9 is terminated or reduced.

Because other components of the structure are almost identical to those of the first embodiment, the detailed explanation thereof will be omitted.

As described above, in the first embodiment (FIG. 2 and FIG. 3) and third embodiment (FIG. 6), a structure was shown in which the movement of the exhalation valve 7 was detected with a sensor, but the mechanism of valve switching detection with the sensor can be also applied to detect the switching of the inhalation valve 8. In this case, however, when the sensor detects that the inhalation valve 8 has been opened, the drive signal is sent to the motor 9 for driving the blower. Further, in the second embodiment, a structure was shown in which the movement of the inhalation valve 8 was detected with a photointerrupter 11, but such a mechanism of valve switching detection can be also applied to detect the switching of the exhalation valve 7. In this case, however, when the photointerrupter 11 detects that the exhalation valve 7 has been closed, the drive signal is sent to the motor 9 for driving the blower.

Test results for the breathing apparatus 1 in accordance with the present invention will be described below with reference to FIGS. 7 through 9.

The increase in the draft resistance of filtration material 15 was studied by using the breathing apparatus 1 in accordance with the present invention and conducting breathing at a rate of 15 times per minute and 0.75 L per inhalation at a dust concentration of 30 mg/m$^3$. For comparison, the draft resistance of the filtration material was studied under identical conditions on the conventional breathing apparatus in which ventilation with the blower was also conducted during exhalation. The test results are shown in FIG. 7.

Figure 7:
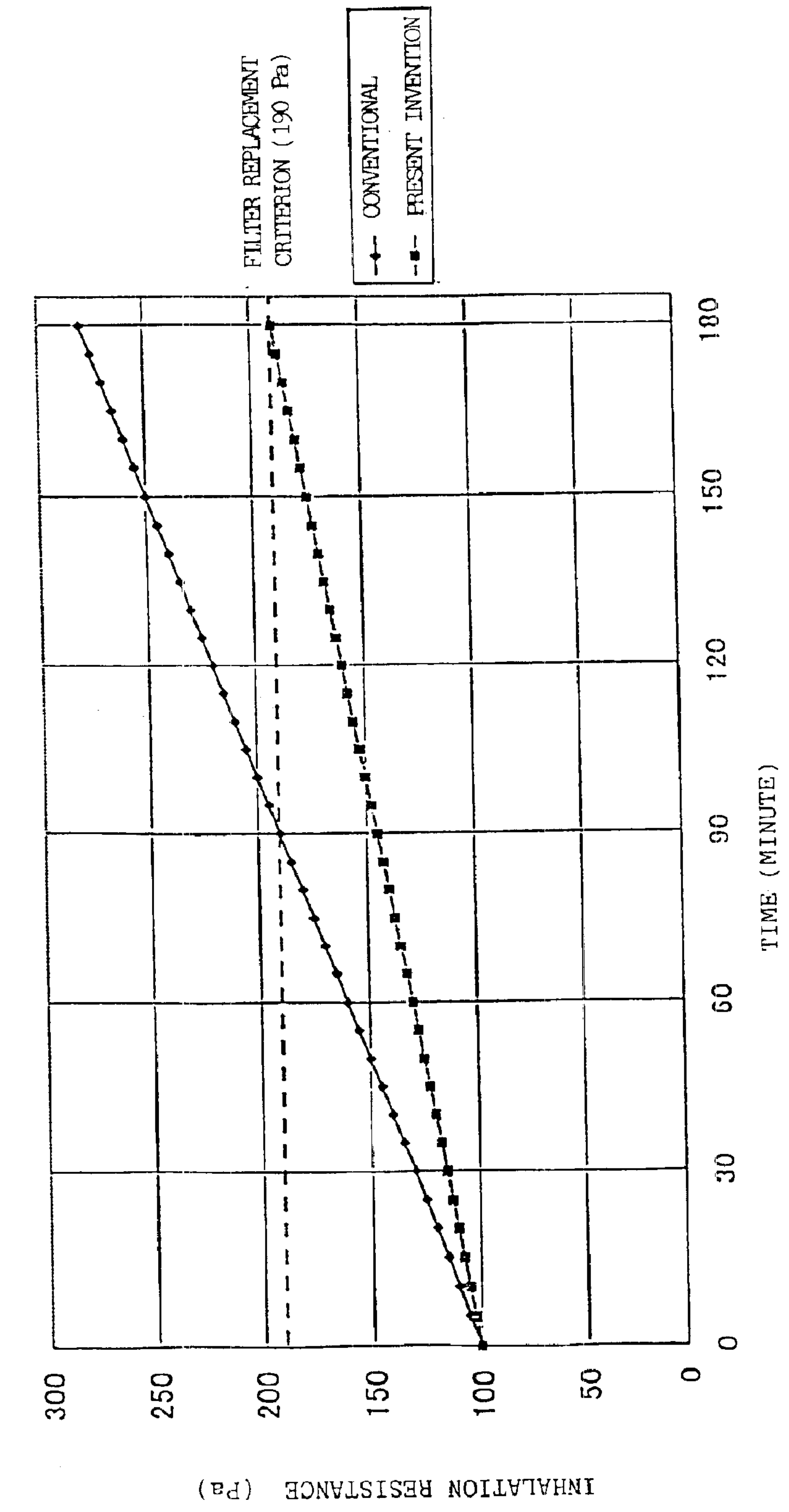
FIG. 7 shows the test results relating to the increase in draft resistance of the filtration material used in the breathing apparatus.
Figure 8:
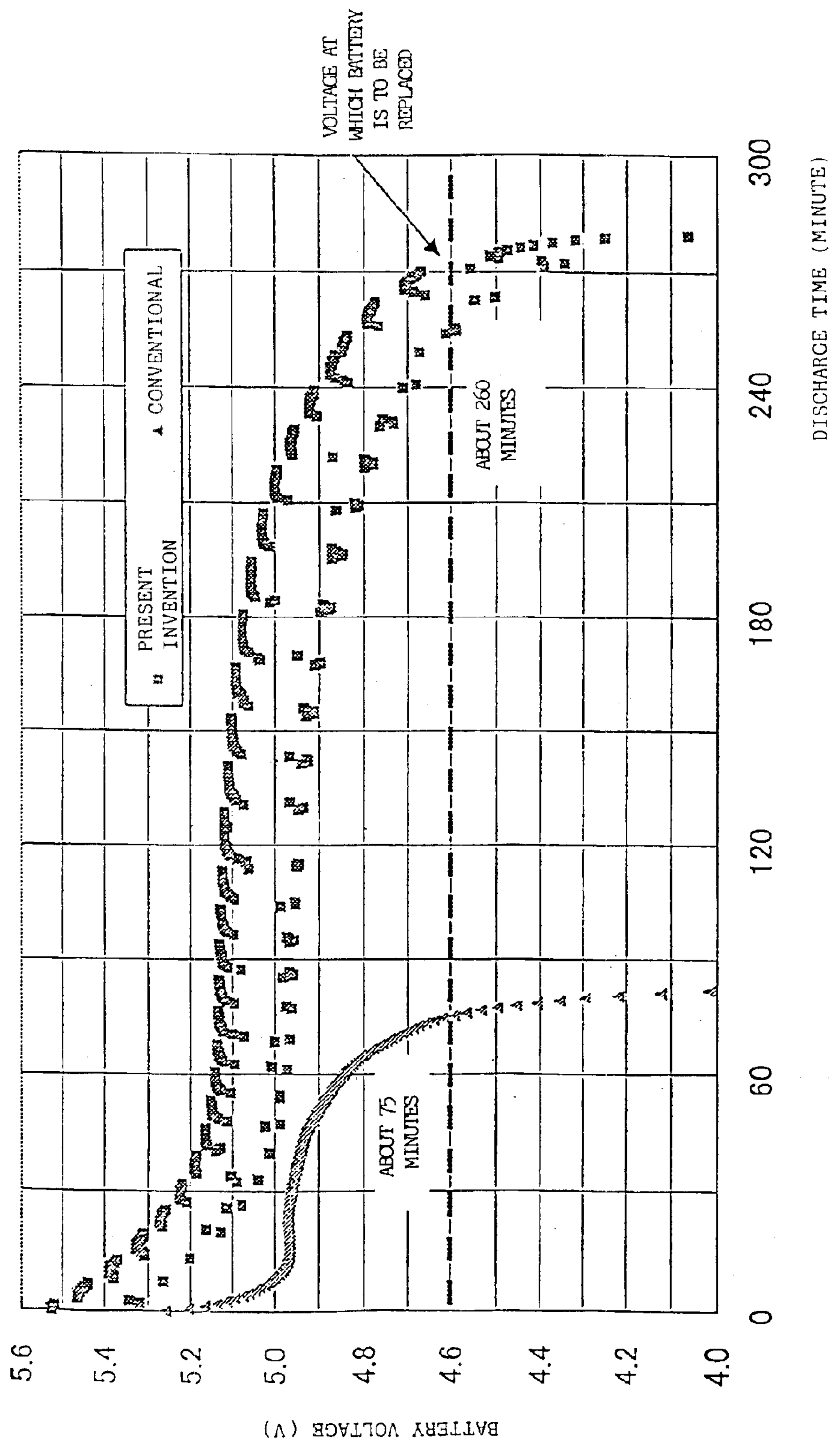
FIG. 8 shows the test results relating to the discharge characteristic of the battery used as a power source for the motor for driving the blower in the breathing apparatus.

As is clear from FIG. 7, the conventional breathing apparatus required only 90 minutes to reach a draft resistance of 190 Pa which is a replacement criterion for the filtration material, whereas in the breathing apparatus 1 in accordance with the present invention, this interval was 180 minutes, that is, twice as long.

The discharge characteristic of the battery serving as a power source of motor 9 in the breathing apparatus 1 in accordance with the present invention and the discharge characteristic of the battery of identical capacity serving as a power source for the motor in the conventional breathing apparatus were studied. The results are shown in FIG. 8.

The test results show that in the conventional breathing apparatus the battery had to be replaced in 75 minutes, whereas in the breathing apparatus 1 in accordance with the present invention, the replacement period was more than 260 minutes, that is, longer by a factor of about 3.5.

Changes in pressure inside the facepiece 2 during breathing were also studied for the breathing apparatus 1 in accordance with the present invention and the conventional breathing apparatus with a constantly operating blower. The test results are shown in FIG. 9.

Figure 9:
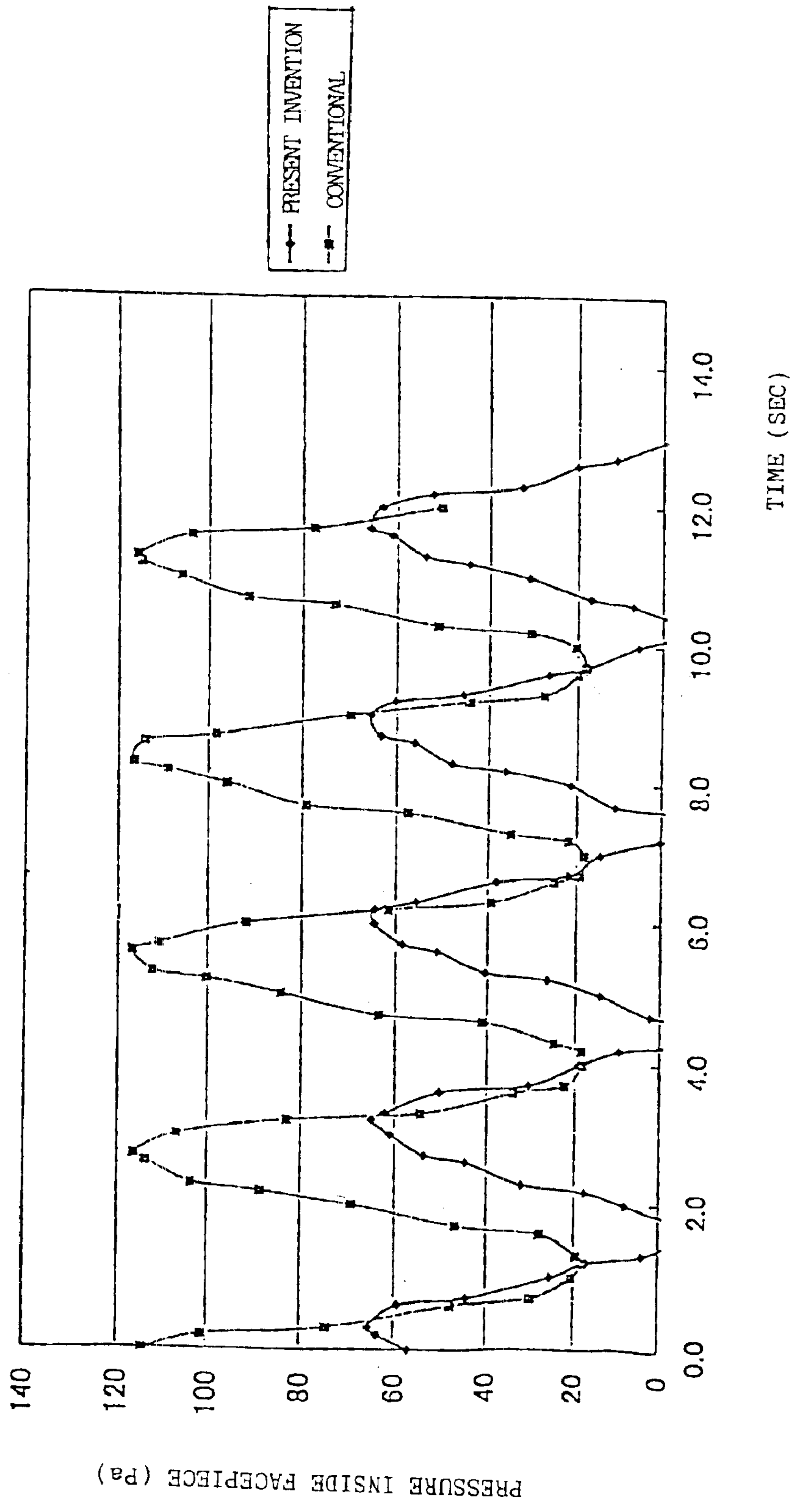
FIG. 9 shows the test results relating to changes in pressure inside the facepiece of the breathing apparatus.

As is clear from FIG. 9, the peak of pressure during exhalation in the facepiece 2 was at 120 Pa in the conventional breathing apparatus and at less than 70 Pa in the breathing apparatus 1 in accordance with the present invention. As a result, it has been established that using the breathing apparatus 1 in accordance with the present invention reduced the exhalation resistance during exhalation by about 40% relative to that of the conventional breathing apparatus.

As described hereinabove, with the present invention, power supply to the motor is terminated or reduced during exhalation when ventilation with the blower is not required. Therefore, the increase in exhaustion of filtration material and power consumption can be suppressed. Moreover, exhalation resistance during exhalation caused by pressure increase inside the facepiece can be decreased.

Further, because the exhalation valve or inhalation valve, which is originally provided in the breathing apparatus, is employed to conduct switching of the blower ventilation linked to breathing, a large number of parts are not necessary and complex air channels are not required. Therefore, the structure can be simple.

Moreover, because a very brittle diaphragm that can be easily ruptured or deformed is not used, the probability of breakdown is reduced and there is no need to worry about the shift in the set value serving as a switching criterion for blower ventilation.

What is claimed is:

1. A breathing apparatus, comprising:

a facepiece with an inhalation opening and an exhalation opening formed therein;

an inhalation valve disposed adjacent to said inhalation opening so as to be open during inhalation and closed during exhalation;

an exhalation valve disposed adjacent to said exhalation opening so as to be closed during inhalation and open during exhalation;

a blower driven by a motor for blowing the outside air into said facepiece through said inhalation opening; and a sensor which is responsive to the opening or closing operation of said exhalation valve or inhalation valve to produce control signals, wherein a power supply to said motor is controlled based on the signals from said sensor.

2. The breathing apparatus according to claim 1, wherein said sensor comprises a photointerrupter disposed in the vicinity of said exhalation valve or inhalation valve for sensing the position of said exhalation valve or inhalation valve.

3. A breathing apparatus, comprising:

a facepiece with an inhalation opening and an exhalation opening formed therein;

an inhalation valve disposed adjacent to said inhalation opening so as to be open during inhalation and closed during exhalation;

an exhalation valve disposed adjacent to said exhalation opening so as to be closed during inhalation and open during exhalation;

a blower driven by a motor for blowing the outside air into said facepiece through said inhalation opening; and a sensor which is sensitive to the opening or closing operation of said exhalation valve or inhalation valve, wherein power supply to said motor is controlled based on the signals from said sensor; and wherein said sensor comprises said exhalation valve or inhalation valve formed from an electrically conductive material and a valve seat formed from an electrically conductive material secured to the facepiece and detects that said exhalation valve or inhalation valve has been closed by sensing the electric current from said exhalation valve or inhalation valve to the valve seat.

* * * * *